United States Patent
Hubel et al.

(10) Patent No.: US 8,518,716 B2
(45) Date of Patent: Aug. 27, 2013

(54) **SOLUBLE CD117 (*SC-KIT*) FOR DIAGNOSIS OF PREECLAMPSIA AND ECLAMPSIA**

(75) Inventors: Carl A. Hubel, Pittsburgh, PA (US); Janet M. Catov, Pittsburgh, PA (US); Robin E. Gandley, Gibsonia, PA (US); James M. Roberts, Pittsburgh, PA (US); Augustine Rajakumar, Ashland, MA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 285 days.

(21) Appl. No.: 12/955,762

(22) Filed: Nov. 29, 2010

(65) Prior Publication Data
US 2011/0129551 A1 Jun. 2, 2011

Related U.S. Application Data

(60) Provisional application No. 61/265,260, filed on Nov. 30, 2009.

(51) Int. Cl.
*G01N 33/53* (2006.01)
(52) U.S. Cl.
USPC ............ 436/814; 435/7.1; 435/7.2; 435/973; 436/65; 436/804; 436/811; 530/352; 530/380; 530/388.7
(58) Field of Classification Search
USPC ................... 435/7.1, 7.2, 7.92; 436/65, 804, 436/814; 530/352, 380, 388.7
See application file for complete search history.

(56) References Cited

PUBLICATIONS

Broudy et al. Human Umbilical Vein Endothelial Cells Display High Affinity c-kit Receptors and Produce a Soluble Form of the c-kit Receptor. Blood 83 (8): 2145-2152 (Apr. 15, 1994).*
Parant et al. CD34+ cells in maternal blood are mainly fetal in origin and express endothelial markers, Laboratory Investigation 89: 915-923 (Jun. 2009 online publication).*
Aicher et al., "Mobilizing endothelial progenitor cells," *Hypertension*, 45(3): 321-325, 2005.
Akin et al., "Soluble stem cell factor receptor (CD117) and IL-2 receptor alpha chain (CD25) levels in the plasma of patients with mastocytosis: Relationships to disease severity and bone marrow pathology," *Blood*, 96(4): 1267-1273, 2000.
Ashman, "The biology of stem cell factor and its receptor C-kit," *Int J Biochem Cell Biol*, 31(10): 1037-1051, 1999.
Barber et al., "The ever-elusive endothelial progenitor cell: identities, functions and clinical implications," *Pediatr Res*, 59(4): 26R-32R, 2006.
Bono et al., "Serum KIT and KIT ligand levels in patients with gastrointestinal stromal tumors treated with imatinib,"*Blood*, 3(8): 2929-2935, 2004.
Broudy et al., "Human umbilical vein endothelial cells display high-affinity c-kit receptors and produce a soluble form of the c-kit receptor," *Blood*, 83(8): 2145-2152, 1994.
Broudy VC, "Stem cell factor and hematopoiesis," *Blood*, 90(4): 1345-1364, 1997.

(Continued)

*Primary Examiner* — Gail R Gabel
(74) *Attorney, Agent, or Firm* — Klarquist Sparkman, LLP

(57) ABSTRACT

This disclosure relates to methods of predicting and diagnosing preeclampsia and eclampsia in pregnant subjects. These methods include detecting a decrease of soluble c-kit in a sample obtained from the pregnant subject. A significantly reduced concentration of soluble c-kit in the sample as compared to a gestational age-adjusted control indicates that the pregnant subject will develop or has preeclampsia or eclampsia.

22 Claims, 5 Drawing Sheets

(56) References Cited

PUBLICATIONS

Chesley LC, "Hypertension in pregnancy: Definitions, familial factor, and remote prognosis," *Kidney Int.* 18: 234-240, 1980.

Cruz et al., "Tumor necrosis factor-alpha-converting enzyme controls surface expression of c-kit and survival of embryonic stem cell-derived mast cells," *Journal of Biology Chemistry*, 279: 5612-5620, 2004.

Gammill et al., "Endothelial progenitor cells and preeclampsia," *Front Biosci*, 12: 2383-2394, 2007.

Germain et al., "Endothelial Dysfunction. A link among preeclampsia, recurrent pregnancy loss, and future cardiovascular events?" *Hypertension*, 49: 90-95, 2007.

Grill et al., "Potential markers of preeclampsia—a review," *Reprod Biol Endocrinol*, 7: 70, 2009 (14 pages).

Hashino et al., "Soluble c-kit levels in acute GVHD after allogeneic bone marrow transplantation," *Br J Haematol*, 89(4): 897-899, 1995.

Jialal et al., "Circulating Levels of Endothelial Progenitor Cell Mobilizing Factors in the Metabolic Syndrome," *The American Journal of Cardiology*, 106(11): 1606-1608, 2010.

Kanbe et al., "Serum levels of stem cell factor and soluble KIT are elevated in patients with atopic soluble dermatitis and correlate with the disease severity," *Br J Dermatol*, 144(6): 1148-1153, 2001.

Karumanchi et al., "Preeclampsia pathogenesis: "triple a rating"—autoantibodies and antiangiogenic factors," *Hypertension*, 51(4): 991-992, 2008.

Kawakita et al., "Soluble c-kit molecule in serum from healthy individuals and patients with haemopoietic disorders," *Br J Haematol.*, 91(1): 23-29, 1995.

Kitoh et al., "Significance of stem cell factor and soluble KIT in patients with systemic lupus erythematosus," *Clin Reheumatol*, 17: 293-300, 1998.

Levine et al., "Soluble endoglin and other circulating antiangiogenic factors in preeclampsia," *N. Engl J Med*, 355(10): 992-1005, 2006.

Luppi et al., "Maternal Circulating CD34+ VEGFR-2+ and CD133+ VEGFR-2+ Progenitor Cells Increase During Normal Pregnancy but Are Reduced in Women With Preeclampsia," *Reproductive Sciences*, 17(7): 643-652, 2010.

Mathew et al., "Placental Growth Factor and Soluble c-Kit Receptor Dynamics Characterize the Cytokine Signature of Imatinib in Prostate Cancer and Bone Metastases," *Journal of Interferon & Cytokine Research*, (e-published ahead of print, Feb. 16, 2011).

Maynard et al., "Soluble Fms-like tyrosine kinase 1 and endothelial dysfunction in the pathogenesis of preeclampsia," *Pediatr Res*, 57(5): 1R-7R, 2005.

Miyanohara et al., "Diagnostic significance of soluble c-kit in the cerebrospinal fluid of patients with germ cell tumors," *J Neurosurg*, 97(1): 177-183, 2002.

Müller-Ehmsen et al., "Decreased Number of circulating progenitor cells in obesity: beneficial effects of weight reduction," *Eur Heart J*, 29(12): 1560-1568, 2008.

Nakamura et al., "Soluble c-kit receptor mobilizes hematopoietic stem cells to peripheral blood in mice," *Exp Hematol.* 32(4): 390-396, 2004.

Ness et al., "Heterogeneous causes constituting the single syndrome of preeclampsia: A hypothesis and its implications," *American Journal of Obstetrics & Gynecology*, 175: 1365-1370, 1996.

Redman et al., "Preeclampsia: An excessive maternal inflammatory response to pregnancy," *American Journal of Obstetrics & Gynecology*, 180(2 Part 1):499-506, 1999.

Roberts et al., "Is oxidative stress the link in the two-stage model of pre-eclampsia?" *Lancet*, 354: 788-789, 1999.

Roberts et al., "Preeclampsia: Recent insights," *Hypertension*, 46(6):1243-1249, 2005.

Roberts JM, "Endothelial Dysfunction in Preeclampsia," *Semin Reprod Endocrinol*, 16(1): 5-15, 1998.

Schatteman et al., "Biology of bone marrow-derived endothelial cell precursors," *Am J Physiol Heart Circ Physiol*, 292(1): H1-8, 2007.

Shibata et al., "Soluble fms-like tyrosine kinase 1 is increased in preeclampsia but not in normotensive pregnancies with small-for-gestational-age neonates: relationship to circulating placental growth factor," *J Clin Endocrinol Metab*, 90(8): 4895-4903, 2005.

Tajima et al., "Serum soluble c-kit receptor and expression of c-kit protein and mRNA in acute myeloid leukemia," *Eur J Haematol*, 60(5): 289-296, 1998.

Venkatesha et al., "Soluble endoglin contributes to the pathogenesis of preeclampsia," *Nat Med*, 12(6): 642-649, 2006.

Walsh, "Obesity: a risk factor for preeclampsia," *Trends Endocrinol Metab*, 18(10): 365-370, 2007.

Westerweel et al., "Endothelial progenitor cell levels in obese men with the metabolic syndrome and the effect of simvastatin monotherapy vs. simvastatin/ezetimibe combination therapy," *Eur Heart J*, 29(22): 2808-2817, 2008.

Woelkers et al., "The endothelium and pre-eclampsia," *In Handbook of Hypertension*, New York: Rubin PC, ed., Elsevier, 21: 126-162, 2000.

Wypych et al., "Soluble kit receptor in human serum," *Blood*, 85(1): 66-73, 1995.

\* cited by examiner

SOLUBLE CD117 (*SC-KIT*) FOR DIAGNOSIS OF PREECLAMPSIA AND ECLAMPSIA

CROSS REFERENCE TO RELATED APPLICATION

This application claims the benefit of U.S. Provisional Application No. 61/265,260, filed Nov. 30, 2009, which is incorporated by reference herein in its entirety.

FIELD

This disclosure relates to methods of predicting and diagnosing preeclampsia and eclampsia in pregnant subjects.

BACKGROUND

Preeclampsia is a hypertensive disorder that occurs only during pregnancy, affecting roughly 5% of all pregnancies. Preeclampsia typically arises after 20 weeks gestation (middle to late pregnancy). It is a rapidly progressive condition characterized by high blood pressure and abnormally high concentrations of protein in the urine. Preeclampsia and other hypertensive disorders of pregnancy are a leading cause of maternal and infant illness and death. By conservative estimates, these disorders are responsible for 76,000 maternal and 500,000 infant deaths each year. The etiology and pathogenesis of preeclampsia remains poorly understood and useful predictors of the disease are currently lacking (Roberts and Hubel, *Lancet*, 354:788-789, 1999).

This disease, or the threat of onset, is the most common cause of elective premature delivery, accounting for approximately 15% of all premature births. The measurement of blood pressure and testing for proteinuria in all pregnant women is carried out predominantly for the detection of preeclampsia. However, these procedures and the care of affected women and of the premature children make considerable demands on healthcare resources. In addition, there is no widely accepted or accurate method for the early prediction of preeclampsia. Elevation of the blood pressure and detection of protein in the urine occur when the disease process is well established.

Detection of an abnormality of the blood flow to the uterine artery by Doppler ultrasound in women who later develop preeclampsia has been of some predictive use but this abnormality has been found to be relatively non-specific. In addition, both sFlt-1 and soluble endoglin were proposed to have potential predictive utility for preeclampsia, but their modest screening performance (sensitivity for detection of impending preeclamptic cases) suggests that while they may not be clinically useful as sole/individual disease predictors. Thus, a need remains for the development of an early pregnancy predictive test for preeclampsia and resultant eclampsia.

SUMMARY OF THE DISCLOSURE

Methods are provided herein for diagnosing or predicting preeclampsia or eclampsia in a pregnant subject. These methods include quantitating soluble c-kit (sc-kit) in a sample from the pregnant subject; wherein the concentration of sc-kit in the sample indicates that the subject has or will develop preeclampsia or eclampsia. The sample can be any sample of interest, for example a bodily fluid that contains sc-kit, including a blood, plasma, serum, or urine sample. In some embodiments, the concentration of sc-kit is compared to a control, such as a standard value, or a sample from a subject known not to have preeclampsia or eclampsia, such as a gestationally-matched subject. In some embodiments, a reduced concentration of sc-kit in the sample as compared to a control indicates that the subject has or will develop preeclampsia or eclampsia. In other embodiments, the methods are utilized prior to, or in conjunction with, detecting increased blood pressure or proteinuria in a pregnant subject.

In some embodiments, the methods disclosed herein can distinguish preeclampsia or eclampsia from gestational hypertension in a pregnant subject. These methods include detecting sc-kit in the sample; wherein the concentration of sc-kit in the sample indicates that the subject has or will develop preeclampsia or eclampsia and does not have gestational hypertension. In some embodiments, the concentration of sc-kit is compared to a control, such as a standard value, or a sample from a subject known not to have preeclampsia or eclampsia or known to have gestational hypertension, such as a gestationally-matched subject. A reduced concentration of sc-kit in the sample as compared to a control indicates that the subject has or will develop preeclampsia or eclampsia and does not have gestational hypertension.

The foregoing and other objects, features, and advantages of the invention will become more apparent from the following detailed description, which proceeds with reference to the accompanying figures.

DETAILED DESCRIPTION

I. Abbreviations

Figure 1:
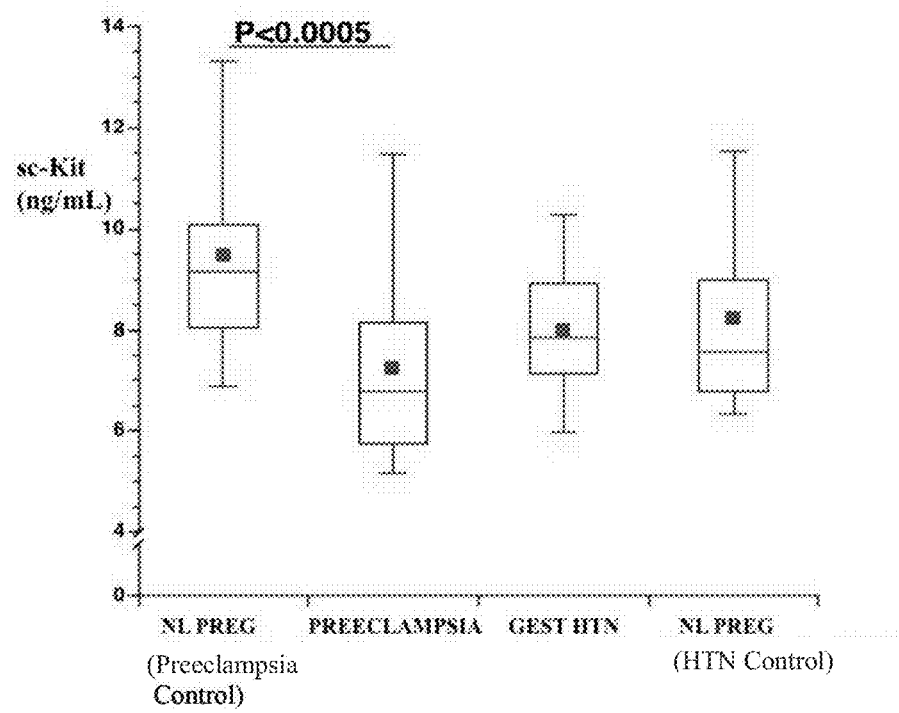
FIG. 1 is a graph showing the results of a cross-sectional study using ELISA to compare the concentration of sc-kit in women diagnosed with preeclampsia and diagnosed with gestational hypertension (GEST HTN). Concentration of sc-kit in women who had normal pregnancies is also shown (NL-PREG) as respective gestationally-matched controls for the preeclamptic and hypertensive test groups.

ANOVA Analysis of variance
AuNP Gold nanoparticles
BMI Body mass index
ELISA Enzyme-linked immunosorbent assay
EPC Endothelial progenitor cell
FACS Fluorescence activated cell sorting
FITC Fluorescein isothiocyanate
HRP Horseradish peroxidase
mRNA Messenger ribonucleic acid
MWCNT Multi-wall carbon nanotubes
PBS Phosphate buffered saline
PlGF Free placental growth factor
RIA Radioimmunoas say
SELDI-TOF Surface-enhanced laser desorption-ionization time-of-flight
SCF Stem cell factor
sc-kit Soluble c-kit
sFlt-1 Soluble fms-like tyrosine kinase-1
SWNT Single-wall carbon nanotubes
VEGFR-1 Vascular endothelial growth factor receptor-1
VEGFR-2 Vascular endothelial growth factor receptor-2

II. Terms

Unless otherwise noted, technical terms are used according to conventional usage. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Terms describing protein structure and structural elements of proteins can be found in Creighton, Proteins, Structures and Molecular Properties, W.H. Freeman & Co., New York, 1993 (ISBN 0-717-7030) which is incorporated by reference herein in its entirety.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All publications, patent applications, patents, and other references mentioned herein are incorporated by reference in their entirety. In case of conflict, the present specification, including explanations of terms, will control. In addition, all the materials, methods, and examples are illustrative and not intended to be limiting. In order to facilitate review of the various embodiments of the disclosure, the following explanations of specific terms are provided:

Alteration: A statistically significant change in a parameter as compared to a control. In one example, an "increase" is a statistically significant elevation in a parameter, such as the presence of a biological marker, such as sc-kit, as compared to a control. Suitable statistical analyses are well known in the art, and include, but are not limited to, Student's T test and ANOVA assays. In some embodiments, an "increase" or "elevation" is about a 10%, 20%, 30%, 40% 50%, 60%, 70%, 80%, 90% or a 2-fold, 3-fold, 4-fold or 5-fold increase. In one example, a "decrease" or "reduction" is a statistically significant decline in a parameter, such as the presence of a biological marker, such as sc-kit, as compared to a control. Suitable statistical analyses are well known in the art, and include, but are not limited to, Student's T test and ANOVA assays. In some embodiments, a "decrease" is about a 10%, 20%, 30%, 40% 50%, 60%, 70%, 80%, 90% or a 2-fold, 3-fold, 4-fold or 5-fold decrease.

Animal: Living multi-cellular vertebrate organisms, a category that includes, for example, mammals and birds. The term mammal includes both human and non-human mammals.

Antibody: A polypeptide substantially encoded by an immunoglobulin gene or immunoglobulin genes, or fragments thereof, which specifically binds an analyte (antigen) such as sc-kit. Immunoglobulin genes include the kappa, lambda, alpha, gamma, delta, epsilon and mu constant region genes, as well as the myriad immunoglobulin variable region genes.

Antibodies exist, for example as intact immunoglobulins and as a number of well characterized fragments produced by digestion with various peptidases. For instance, Fabs, Fvs, and single-chain Fvs (SCFvs) that specifically bind to sc-kit or fragments of sc-kit would be sc-kit-specific binding agents. This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (such as humanized murine antibodies), heteroconjugate antibodies such as bispecific antibodies). See also, *Pierce Catalog and Handbook*, 1994-1995 (Pierce Chemical Co., Rockford, Ill.); Kuby, *J., Immunology*, 3$^{rd}$ Ed., W.H. Freeman & Co., New York, 1997.

Antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. The term "antibody," as used herein, also includes antibody fragments either produced by the modification of whole antibodies or those synthesized de novo using recombinant DNA methodologies.

Typically, a naturally occurring immunoglobulin has heavy (H) chains and light (L) chains interconnected by disulfide bonds. There are two types of light chain, lambda ($\lambda$) and kappa ($\kappa$). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example, see U.S. Pat. No. 5,585,089).

Control: A value used as a source for comparison with an experimentally determined value. A control can be a standard value, a concentration (such as of a soluble factor or circulating concentration of cells) from one subject, or averaged from many subjects, who does not have a known disorder (such as preeclampsia or eclampsia), or a baseline concentration obtained from a subject at an earlier time point. Controls for gestational values can be adjusted for stage of gestation, which is referred to as a gestational age-adjusted control.

Detecting or determining: Detection refers to identifying the presence of a target molecule in a sample. Determining refers to quantitating the target molecule in the sample, either absolutely or relatively. For example, sc-kit can be detected or determined in a sample from a pregnant subject, such as a blood, plasma, serum, or urine sample. Generally, detecting or determining a biological molecule, such as a protein, nucleic acid, or specific cell type in the blood, requires performing a biological assay and not simple observation. For example, assays that utilize antibodies or nucleic acid probes (which can both be labeled) can be used to detect or determine proteins or nucleic acids, respectively. Diagnosing or diagnosis of preeclampsia/eclampsia involves detecting a concentration of sc-kit in a blood, plasma, serum, or urine sample from a pregnant subject, such as a concentration that is reduced as compared to a control.

Endothelial Progenitor Cell (EPC): Cell type with the potential to differentiate into mature endothelial cells and participate in new blood vessel formation. EPCs can also support the ongoing function of mature endothelial cells by providing growth factors and other paracrine signals. Endothelial progenitor cells are mobilized into the blood circulation in response to growth factors such as VEGF. EPCs can be identified, for example, by the presence of CD34, CD133, CD117, the vascular endothelial growth factor receptor-2 (VEGFR-2) and CD31 and the absence or low levels of detectable CD45.

Fms-like tyrosine kinase-1 (Flt-1): Also known as VEGF receptor-1, the soluble form, sFlt-1, is an anti-angiogenic factor that is increased in most women with preeclampsia. sFlt-1 binds to, and thus neutralizes, VEGF and PlGF. An exemplary protein sequence for Flt-1 is found at GEN-BANK® accession number NM_002019 (accessed on Nov. 29, 2009).

Free placental growth factor (PlGF): A pro-angiogenic factor that has been shown to be reduced in preeclamptic subjects. An exemplary protein sequence for PlGF is found at GENBANK® accession number NM_002632 (accessed on Nov. 29, 2009).

Gestational hypertension (Pregnancy-induced hypertension): Hypertension associated with pregnancy, but without concurrent high concentrations of protein in urine. For a diagnosis of gestational hypertension to be made, the patient must have been normotensive before becoming pregnant and must have a blood pressure of at least 140 sytolic and/or at least 90 mm Hg diastolic, arising de novo after 20 weeks gestation at least two times and at least six hours apart. Women who develop mild gestational hypertension after 37 weeks gestation generally have pregnancy outcomes similar to those of pregnant women who are normotensive, apart from increased rates of induced labor and cesarean delivery.

Gestationally-matched: A "gestationally-matched" or "gestational age-adjusted" sample is a sample type that is taken from pregnant subjects at about the same time point during pregnancy. For example, a gestationally-matched control blood sample is a blood sample taken from a control individual (such as an individual experiencing a normal pregnancy) at about the same or similar gestational time that a blood sample is taken from a test individual (such as to determine if the individual has preeclampsia).

Hypertension: A subject is considered to be hypertensive, or have hypertension if measured systolic blood pressure is about 140 mm Hg or greater and/or measured diastolic blood pressure is about 90 mm Hg or greater. Prehypertension consists of blood pressure that is 120 to 139 mm Hg (systolic) and 80 to 89 mm Hg (diastolic).

Immunoassay: A method of detecting the presence or amount of a protein (as opposed to an mRNA encoding a protein) in a sample. An immunoassay detects a protein (for example, an antigen, such as sc-kit) in a sample by detecting interaction of the antigen with a specific binding agent, such as an antibody. A sample including an antigen (such as sc-kit) is incubated with an antibody under conditions permitting antibody-antigen binding. Antibody-antigen binding can be detected by means of a detectable label conjugated to the antibody (such as a primary antibody), by means of a detectable label conjugated to a secondary antibody, which is raised against the primary antibody, or by means of a detectable label conjugated directly or indirectly to a second antibody that binds the antigen. Exemplary detectable labels that can be used for immunoassays include, but are not limited to, radioactive isotopes, fluorochromes (such as fluorescein, fluorescein isothiocyanate, and rhodamine), magnetic labels, and enzymes (such as horseradish peroxidase or alkaline phosphatase). Particular examples of immunoassays include without limitation, ELISA, Western blotting, immunohistochemistry, electrochemical immunoassay, radioimmunoassay, and magnetic immunoassay. In a specific non-limiting example, an immunoassay used to detect sc-kit protein includes a conventional ELISA utilizing an anti-sc-kit antibody (for example, anti-human sc-kit, such one commercially available from R&D Systems, Minneapolis, Minn.).

Immunologically reactive conditions: Includes "conditions sufficient to form an immune complex" which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols (such as ELISA or radioimmunoassay) or those conditions encountered in vivo. See Harlow & Lane, Antibodies, *A Laboratory Manual*, Cold Spring Harbor Publications, New York (1988), for a description of immunoassay formats and conditions. The immunologically reactive conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Normotensive: Having a normal blood pressure. Normotenisive is generally considered to be a systolic blood pressure of 90-120 mm Hg and a diastolic blood pressure of 60-79 mm Hg.

Prediction: Determination that a subject who does not manifest symptoms of a given disease will develop the disease. In particular examples, it is possible to predict that a pregnant subject will develop preeclampsia/eclampsia during the pregnancy by the measurement of a significant reduction of sc-kit in the pregnant subject in comparison to a control.

Preeclampsia: A hypertensive disorder that occurs only during pregnancy. In human subjects, preeclampsia typically arises after 20 weeks gestation (middle to late pregnancy). It is a rapidly progressive condition characterized by hypertension and abnormally high concentration of protein in the urine. Left untreated, preeclampsia can develop into the more severe form of the disorder known as eclampsia, which is additionally characterized by seizures and possible coma and death.

Preeclampsia has been classically diagnosed by a clinician according to the guidelines of the International Society for the Study of Hypertension in Pregnancy (Davey et al., *Am. J. Obstet Gynecol*; 158: 892-98, 1988). Gestational hypertension is diagnosed as two recordings of diastolic blood pressure of 90 mm Hg or higher at least 4 hours apart and is considered severe if the diastolic pressure is 110 mm Hg or higher at least 4 hours apart or one recording of diastolic blood pressure of at least 120 mm Hg. Proteinuria is diagnosed as excretion of 300 mg or more in 24 hours or two readings of 2+ or higher on dipstick analysis of midstream or catheter urine specimens if no 24 hour collection was available. Women are classified as previously normotensive or with chronic hypertension before 20 weeks' gestation. For previously normotensive women, preeclampsia is diagnosed as gestational hypertension with proteinuria. For women with chronic hypertension, superimposed preeclampsia is often diagnosed by the new development of proteinuria.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation.

Sample: A biological specimen containing genomic DNA, RNA (including mRNA), protein, or combinations thereof, obtained from a subject. In some examples, a sample is a bodily fluid, such as, but not limited to, a blood, serum, plasma, urine or saliva sample. A bodily fluid is a natural liquid or secretion of a subject's body.

Soluble c-kit (sc-kit): Soluble form of c-kit [sc-kit, also known as stem cell factor soluble receptor (SCFsR), or soluble CD117]. As described herein, sc-kit is significantly reduced in a sample, such as a blood, plasma, serum, or urine sample, of preeclamptic subjects compared to control pregnant subjects.

C-kit is a receptor tyrosine kinase expressed in many cell types of the hematopoietic hierarchy as well as some mature natural killer cells, germ cells, melanocytes, glial cells, smooth muscle cells, endothelial progenitor cells (EPCs), some mature endothelial cells, and placenta. The c-kit gene encodes a 972 amino acid precursor protein; the N-terminal 25 amino acids of which are a signal peptide, followed by a 495 amino acid extracellular domain, a 23 amino acid transmembrane domain and a 429 amino acid cytoplasmic domain. Proteolytic cleavage of c-kit releases its extracellular domain and is known as sc-kit. An exemplary sequence of the full-length c-kit protein is found at GENBANK® accession number NM_000222 (accessed on Nov. 29, 2009).

Soluble endoglin: A truncated, circulating version of the normally membrane-bound endoglin receptor. It increases in maternal blood months before the clinical signs of preeclampsia manifest. An exemplary sequence of the endoglin protein is found at GENBANK® accession number is NM_000118 (accessed on Nov. 29, 2009).

Specifically binds: A term that refers to the binding of agent that preferentially binds to a defined target (such as an antibody to a specific antigen or a nucleic acid probe to a specific nucleic acid sequence). With respect to an antigen, "specifically binds" refers to the preferential association of an antibody or other ligand, in whole or part, with a specific polypeptide (such as sc-kit or a portion thereof).

Standard: A substance or solution of a substance of known amount, purity or concentration that is useful as a control. A standard can also be a known value or concentration of a particular substance. A standard can be compared (such as by spectrometric, chromatographic, spectrophotometric, or statistical analysis) to an unknown sample (of the same or similar substance) to determine the presence of the substance in the sample and/or determine the amount, purity or concentration of the unknown sample. In one embodiment, a standard is a peptide standard. In another embodiment, a standard is a known concentration of sc-kit that is found in a sample from a non-preeclamptic or non-eclamptic subject at a particular gestational age.

Stem Cell Factor (SCF): Also known as kit ligand, mast cell growth factor, or steel factor, SCF is a cytokine that is produced constitutively by bone marrow stromal cells particularly fibroblasts and by endothelial cells as both a transmembrane form and as a secreted/soluble from (by alternative splicing). SCF triggers its biologic activity by binding to its membrane receptor, c-kit. An exemplary protein sequences for kit ligand variant a (5351 bp) is found at GENBANK® accession number NM_003994 and an exemplary protein sequence for kit ligand variant b (5435 bp) is NM_000899. Both accession numbers were accessed on Nov. 29, 2009.

Subject: Living organisms susceptible to preeclampsia/eclampsia; a category that includes both human and non-human mammals, such as non-human primates.

Under conditions sufficient for: A phrase that is used to describe any environment that permits the desired activity.

III. Overview of Several Embodiments

Disclosed herein are methods of predicting or diagnosing preeclampsia or eclampsia in a pregnant subject. These methods include quantitating soluble c-kit (also referred to herein as sc-kit) in a sample obtained from a pregnant subject. In some embodiments, the sample is a bodily fluid that contains soluble c-kit, such as a blood, plasma, or serum sample. In other embodiments, the sample is a urine or saliva sample. In other embodiments, a reduced concentration of soluble c-kit as compared to a control, such as a gestational age-adjusted control, indicates that the pregnant subject will develop or has preeclampsia or eclampsia. These methods can also include obtaining the sample, preparing a treatment plan based on the assay, or treating the subject for preeclampsia or exlampsia.

In particular embodiments, the disclosed methods can distinguish preeclampsia or eclampsia from gestational hypertension in a pregnant subject. These methods include determining soluble c-kit in a sample from a pregnant subject. In some embodiments, the sample is a bodily fluid, such as a blood, plasma, or serum sample. In other embodiments, the sample is a urine sample or saliva sample. In some embodiments, a reduced concentration of soluble c-kit as compared to a control, such as a gestational age-adjusted control, indicates that the pregnant subject will develop or has preeclampsia or eclampsia and does not have gestational hypertension. These methods can also include obtaining sample.

In particular examples of the disclosed methods, the pregnant subject is a veterinary subject. In other particular examples, the pregnant subject is a human subject, who in further examples is in the second or third trimester of pregnancy, and in still further examples is at least eighteen weeks pregnant.

In some embodiments of the disclosed methods, the control is the concentration of soluble c-kit in a sample from a pregnant subject that does not have preeclampsia or eclampsia. In other embodiments, the control is the concentration of soluble c-kit is a sample from a gestationally-matched pregnant subject that does not have preeclampsia or eclampsia. In other embodiments, the control is a standard value.

In particular examples, the sample is a maternal blood, plasma, or serum sample. In still other examples, the sample is an umbilical cord blood, plasma, or serum sample.

In some embodiments, quantitating soluble c-kit comprises contacting the sample, such as the bodily fluid that contains soluble c-kit, for example blood, plasma, serum, or urine with an antibody that specifically recognizes soluble c-kit, under conditions sufficient to form an immune complex, and determining the presence of the immune complex. In some examples, the antibody is labeled, such as with a radioisotope or an enzyme. In particular examples, quantitating comprises the use of radioimmunoassay (RIA) or the use of an enzyme linked immunosorbant assay (ELISA).

In particular embodiments, the methods described herein can further comprise quantitating soluble fms-like tyrosine kinase-1, soluble endoglin, or free placental growth factor in the sample, wherein a significant elevation in at least one of soluble fms-like tyrosine kinase-1 or soluble endoglin; and/or or a significant reduction in free placental growth factor, in the sample compared with a control indicates the pregnant subject has preeclampsia or eclampsia.

In other embodiments, the methods described herein can further comprise quantitating circulating endothelial progenitor cells in the blood, plasma, or serum sample from the subject, wherein a significant reduction in circulating endothelial progenitor cells compared with the control indicates the pregnant subject has preeclampsia or eclampsia. In such embodiments, quantitating circulating endothelial progenitor cells comprises contacting a blood sample with an antibody, under conditions sufficient to form an immune complex with an endothelial progenitor cell marker, and determining the presence of the immune complex. In particular examples, the endothelial progenitor cell marker is one or more of CD34, CD133, CD117, the vascular endothelial growth factor receptor-2 (VEGFR-2), or CD31.

IV. Methods of Predicting or Diagnosing Preeclampsia/Eclampsia

Preeclampsia is a disease of pregnancy characterized by hypertension and abnormally high concentrations of protein in urine (proteinuria). Left untreated, it can develop into eclampsia, and associated multiple organ system disfunction and potentially death (Grill et al. *Reprod. Biol. Endocrinol.* 7:70, 2009). It is disclosed herein that the concentration of sc-kit is significantly reduced in a preeclamptic/eclamptic pregnant subject in comparison to control sc-kit concentrations, such as in non-preeclamptic/eclamptic pregnant subjects. Thus, preeclampsia/eclampsia can be predicted or diagnosed in a pregnant subject by the measurement of sc-kit in a sample taken from a pregnant subject. The measured concentration of sc-kit can be compared to a control. A significant reduction in sc-kit diagnoses or predicts the development of preeclampsia/eclampsia in the pregnant subject. Measurement of sc-kit concentrations can also be used to distinguish between preeclampsia/eclampsia and gestational hypertension in a subject.

c-Kit and Kit Ligand

The methods of prediction and diagnosis of preeclampsia/eclampsia described herein involve the determination of the circulating concentration of sc-kit in a pregnant subject. Generally, molecular assays are used for the determination of the circulating concentration of sc-kit in a pregnant subject.

Several cytokines/growth factors promote the survival, proliferation, and differentiation of hematopoietic stem cells and progenitor cells both during development in utero (essential) and in adult life (where deficiency of these cells causes pancytopenia and decreases bone marrow cellularity) (Broudy, *Blood*, 90(4):1345-1364, 1997). One of these factors is Stem Cell Factor (SCF; also known as kit ligand, mast cell growth factor, or steel factor). SCF is produced constitutively by bone marrow stromal cells, particularly fibroblasts, and by endothelial cells in both a transmembrane form and as a secreted/soluble from (by alternative splicing). SCF triggers its biologic activity by binding to its membrane receptor, c-kit (also known as stem cell factor receptor, SCFsR, or CD117).

C-kit is a receptor tyrosine kinase expressed in many cell types of the hematopoietic hierarchy as well as some mature natural killer (NK) cells, germ cells, melanocytes, glial cells, smooth muscle cells, endothelial progenitor cells (EPCs), some mature endothelial cells, and placenta (Broudy et al., *Blood*, 83(8):2145-2152, 1994; Ashman, *Int. J. Biochem Cell Biol*, 31(10):1037-1051, 1999). In vivo, binding of SCF to c-kit causes receptor dimerization and activation of tyrosine kinase activity, leading to phosphorylation of the receptor subunits as well as of downstream signal transduction molecules. Uncontrolled activity of c-kit contributes to the formation of various malignancies (Broudy, *Blood*, 90(4):1345-1364, 1997; Broudy et al., *Blood,* 83(8):2145-2152, 1994; Ashman, *Int. J. Biochem Cell Biol*, 31(10):1037-1051, 1999; Wypych et al., *Blood*, 85(1):66-73, 1995; Nakamura et al., *Exp Hematol*, 32(4):390-396, 2004; Cruz et al., *Journal Biol Chem*, 279:5612-5620, 2004).

A soluble form of the c-kit receptor, sc-kit, is generated by proteolytic release of the c-kit extracellular domain (by tumor necrosis factor a-converting enzyme (TACE; ADAM-17)), and can be measured in blood, plasma, or serum (Ashman, *Int J Biochem Cell Biol*, 31(10):1037-1051, 1999; Cruz et al., *Journal Biol Chem*, 279:5612-5620, 2004). sc-kit binds SCF with high affinity and blocks binding of SCF to cell-surface c-kit (Ashman, *Int J Biochem Cell Biol*, 31(10):1037-1051, 1999).

Samples Taken from a Pregnant Subject

As described herein, prediction of the development, or diagnosis of, preeclampsia/eclampsia involves determination of the sc-kit concentration in a sample, for example a bodily fluid, such as a blood, plasma, serum, saliva or urine sample taken from a pregnant subject. Methods of obtaining a blood sample or a fraction thereof (such as plasma or serum), or a urine sample, or a fraction thereof, are routine. In some examples, the blood, plasma, or serum sample is a maternal sample. In other examples, the blood, plasma, or serum sample is a sample from the fetus (such as an umbilical cord blood, plasma or serum sample).

If desired, the sample can be concentrated or purified before use. For example, proteins or nucleic acids can be isolated from the sample. Alternatively, the sample can be used directly. In particular examples, a blood, plasma, serum, or urine sample obtained from a pregnant subject is analyzed to determine the concentration of sc-kit. In other examples the sample is also analyzed to determine the concentration or one or more of sFlt-1, PlGF, soluble endoglin. In other examples the blood sample is also analyzed to determine the number of circulating EPCs.

The subject can be any animal, human or veterinary subject that can become preeclamptic/eclamptic. In particular examples, the subject is a rat, mouse, cow, dog, guinea pig, rabbit, or primate. In one embodiment, the primate is a non-human primate such as a macaque or chimpanzee. In other embodiments, the primate is human.

The typical duration of a human pregnancy is 40 weeks, which is divided into three trimesters. The first trimester is the period from fertilization until 13 weeks after fertilization. The second trimester is the period from 14 weeks until 27 weeks. The third trimester is from 28 weeks until birth. In human subjects, the sample, such as a blood, serum, plasma, or urine sample, is taken from the pregnant subject generally in the second or third trimester of pregnancy. In some embodiments, the sample is taken from the pregnant subject from 4 to 13 weeks, 11 to 24 weeks, 14 to 27 weeks, 27 to 42 weeks, 20 to 25 weeks, 26 to 30 weeks, 31 to 35 weeks, 36 to 40 weeks or 40 to 42 weeks into pregnancy. For example, the sample can be taken from the pregnant subject at 4 to 13 weeks, such as at 5 to 12 weeks, or at 14 to 20 weeks, such as at 16 to 19 weeks; or at 20 to 27 weeks, such as at 22 to 27 weeks into pregnancy. In particular examples, the sample is taken from the pregnant subject at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, or at least 42 weeks into pregnancy. In still other examples, the sample is taken from the pregnant subject at 18, 19, 20, 21, 22, 23, 24, 25, 26, 27, 28, 29, 30, 31, 32, 33, 34, 35, 36, 37, 38, 39, 40, 41, or 42 weeks into pregnancy.

Generally, the concentration of sc-kit in the sample from the pregnant subject is compared to a control. The control can be the concentration of sc-kit in a sample from a subject known not to have preeclampsia or eclampsia. The control can be the concentration of sc-kit from a pregnant subject known not to have preeclampsia or eclampsia, and who is at the same stage of pregnancy (gestationally-matched). The control can also be a standard value, such as a numerical representation of an averaged value of the concentration of sc-kit in samples from pregnant subjects, including gestationally matched subject, known not to have preeclampsia or eclampsia, or an averaged value of the concentration of sc-kit in samples from other subjects, such as women who are not pregnant.

In particular embodiments, the control is a known cut-off value representing a normal concentration of sc-kit in a pregnant subject experiencing a normal pregnancy at a particular time during pregnancy. In these embodiments, a gestationally-matched concentration of sc-kit in the test subject below this value is predictive or determines that the subject will develop or has preeclampsia/eclampsia.

Monitoring the Effectiveness of Therapy

In several embodiments, the diagnostic methods disclosed herein are used for monitoring the usefulness of a specific therapeutic agent administered to a subject. In other embodiments, the methods are used to monitor the usefulness of a therapeutic regimen prescribed for and undertaken by a subject including but not limited to bed rest, dietary restrictions, antihypertensive therapy, or administration of an agent including but not limited to magnesium sulfate. For example, the assays can be performed about every 12, 24, 36, 48, 60, or 72 hours for a specified period, such as daily, biweekly, weekly, or longer.

In some examples, the concentration of sc-kit is assessed. Generally, the therapy or regimen is effective if the concentration of sc-kit increases over time, remains constant or decreases less rapidly over time during the period wherein the therapeutic agent is administered or regiment is undertaken. In contrast, the therapeutic agent is ineffective when the decrease in concentration of sc-kit with time is not attenuated. In this manner, the effectiveness of a particular therapeutic regimen can be assessed.

In one embodiment, the pregnant subject is prescribed a therapeutic protocol. The concentration of sc-kit in a sample from the subject is then assessed. An increase or no change in the concentration of sc-kit, as compared to concentration of sc-kit in a sample from the subject prior to the prescription of the therapeutic protocol (or to a standard value) indicates that the therapeutic protocol in effective in preventing or treating preeclampsia. A continued decrease in the concentration of sc-kit as compared to the concentration of sc-kit in a sample from the subject prior to the administration of the therapeutic protocol (or to a standard value) indicates that the therapeutic protocol is ineffective.

Detection of sc-Kit

Generally, the detection of sc-kit involves the use of molecular methods and the detection of a signal, such as fluorescent, radioactive, or enzymatic readout. Methods of detecting proteins, such as sc-kit, are known in the art. In some examples, immunoassays are used to determine the quantity of sc-kit in a sample, for example a bodily fluid that contains sc-kit, such as a blood, plasma, serum, saliva or urine sample. See Harlow & Lane, Antibodies, *A Laboratory Manual*, Cold Spring Harbor Publications, New York (1988), for a description of immunoassay formats and conditions that can be used to determine specific immunoreactivity. Generally, immunoassays include the use of one or more specific binding agents (such as antibodies) that specifically recognizes and can bind a molecule of interest, such as sc-kit. Such binding agents can include a detectable label (such as a radiolabel, fluorophore or enzyme), that permits detection of the binding to the protein and determination of relative or absolute quantities of the molecule of interest in the sample. Although the details of the immunoassays may vary with the particular format employed, the method of detecting sc-kit in a sample generally includes the steps of contacting the sample with an antibody, which specifically binds to sc-kit under immunologically reactive conditions to form an immune complex between the antibody and sc-kit, and detecting the presence of and/or quantity of the immune complex (bound antibody), either directly or indirectly. Exemplary immunoassays that can be used include, but are not limited to: Western blotting, ELISA, radioimmunoassay, fluorescence microscopy, and flow cytometry.

In one example, the specific binding agent is an antibody, such as a polyclonal or monoclonal antibody, or fragment thereof. In some examples, the antibody is a humanized antibody. In some examples, the antibody is a chimeric antibody.

In one embodiment, the antibody used for detection and quantitation of sc-kit is directly labeled with a detectable label. In another embodiment, the antibody that binds sc-kit, (the first antibody) is unlabeled and a second antibody or other molecule that can bind the antibody that binds sc-kit is utilized. As is well known to one of skill in the art, a second antibody is chosen that is able to specifically bind the specific species and class of the first antibody. For example, if the first antibody is a mouse IgG, then the secondary antibody may be a goat anti-mouse-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

In another example, a sandwich ELISA can be used to detect the presence or determine the amount of an antigen in a sample, such as a sc-kit. In this method, a solid surface is first coated with a sc-kit antibody. The test sample containing the antigen (such as a blood, plasma, serum, or urine sample), is then added and the antigen is allowed to react with the bound antibody. Any unbound antigen is washed away. A known amount of enzyme-labeled sc-kit antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the quantity of sc-kit present in the sample tested.

In an alternative example, sc-kit protein can be assayed in a biological sample by a competition immunoassay utilizing sc-kit protein standards labeled with a detectable substance and an unlabeled antibody that specifically binds sc-kit. In this assay, the biological sample (such as a blood, plasma, serum, or urine sample), the labeled sc-kit protein standards and the antibody that specifically binds sc-kit are combined and the amount of labeled sc-kit standard bound to the unlabeled antibody is determined. The amount of sc-kit protein in the biological sample is inversely proportional to the amount of labeled sc-kit protein standard bound to the antibody that specifically binds sc-kit.

Quantitative spectroscopic methods, such as MALDI or SELDI, can also be used to analyze sc-kit protein amount in a sample (such as a blood, plasma, serum, or urine sample). In one example, surface-enhanced laser desorption-ionization time-of-flight (SELDI-TOF) mass spectrometry is used to detect protein, for example by using the PROTEINCHIP™ detection system (Ciphergen Biosystems, Palo Alto, Calif.). Such methods are well known in the art (for example see U.S. Pat. Nos. 5,719,060, 6,897,072, and 6,881,586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as sc-kit protein. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as sc-kit protein) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector.

In an additional example, the method may include detection of sc-kit protein in a sample using an electrochemical immunoassay method. See, e.g., Yu et al., *J. Am. Chem. Soc.*, 128:11199-11205, 2006; Mani et al., *ACS Nano*, 3:585-594, 2009; Malhotra et al., *Anal. Chem.*, 82:3118-3123, 2010. In this method, an antibody (such as an anti-sc-kit antibody) is conjugated to terminally carboxylated single-wall carbon nanotubes (SWNT), multi-wall carbon nanotubes (MWCNT), or gold nanoparticles (AuNP), which are attached to a conductive surface. A sample (such as a blood, plasma or serum sample) is contacted with the SWNTs, MWCNTs, or AuNPs, and protein in the sample (such as sc-kit) binds to the primary antibody (such as an anti-sc-kit antibody). A second antibody conjugated directly or indirectly to a redox enzyme (such as horseradish peroxidase (HRP), cytochrome c, myoglobin, or glucose oxidase) binds to the primary antibody or to sc-kit protein (for example, in a "sandwich" assay). In some examples, the second antibody is conjugated to the enzyme. In other examples, the second antibody and the enzyme are both conjugated to a support (such as a magnetic bead). Signals are generated by adding enzyme substrate (e.g. hydrogen peroxide if the enzyme is HRP) to the solution bathing the sensor and measuring the current produced by the catalytic reduction.

In a particular example, the method includes a first sc-kit antibody attached to a AuNP sensor surface. A sample (such as a blood, plasma, serum, or urine sample) is contacted with the AuNP sensor including the first antibody. After sc-kit binds to the first (capture) antibody (Ab1) on the electrode, a horseradish peroxidase (HRP)-labeled second sc-kit antibody (HRP-Ab2) or beads conjugated to both a second sc-kit antibody and HRP are incubated with the sensor, allowing the second antibody to bind to sc-kit. Biocatalytic electrochemical reduction produces a signal via reduction of peroxide activated enzyme following addition of hydrogen peroxide. Use of HRP is advantageous for arrays since immobilization of the electroactive enzyme label on the electrode eliminates electrochemical crosstalk between array elements, which can occur when detecting soluble electroactive product.

The concentration of sc-kit detected is compared to a control, such as the concentration of sc-kit in a non-preeclamptic/eclamptic pregnant subject. In some examples, the control can be the concentration of sc-kit from a pregnant subject of the same gestational age known not to have preeclampsia or eclampsia. In other examples, the control is a standard value, such as a value that represents an average concentration of sc-kit expected in a pregnant subject who does not have preeclampsia/eclampsia. In other examples, the standard is the concentration of sc-kit in a non-pregnant subject. Sc-kit is significantly reduced in preeclamptic/eclamptic subjects. Thus, any significant reduction of sc-kit in the blood, plasma, or serum sample of the pregnant subject in comparison to the control will be predictive or indicative of preeclampsia/eclampsia in the subject.

Combination Methods

Methods of prediction and diagnosis of preeclampsia/eclampsia by quantitating sc-kit in a sample (such as a blood, plasma, serum, or urine sample) can be combined with detecting and/or quantitating one or more additional factors the same sample by the methods described above for detection of sc-kit. In particular examples, preeclampsia/eclampsia is predicted or diagnosed in a subject if a sample from the subject has a significantly reduced concentration of sc-kit and one of a significantly increased concentration of sFlt-1 or soluble endoglin, or a significantly reduced concentration of PlGF.

Methods of predicting or diagnosing preeclampsia/eclampsia by measurement of sc-kit also can be combined with measurement of circulating EPCs in the sample. In such embodiments, a significant reduction in circulating EPCs concomitant with a significant reduction in sc-kit will predict or diagnose preeclampsia/eclampsia in the subject.

EPCs are measured in a sample by determining the presence or absence of an EPC-specific cell surface marker, such as CD34, CD133, the vascular endothelial growth factor receptor-2 (VEGFR-2), or CD31. Methods of determining the presence or absence of a cell surface marker are well known in the art and are analogous to the methods of detecting a specific protein in a sample. For example, antibodies that specifically bind to the particular marker can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbent assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort or enumerate cells (see U.S. Pat. No. 5,061,620). Any of the human antibodies that specifically bind CD34, CD133, the vascular endothelial growth factor receptor-2 (VEGFR-2), or CD31, as disclosed herein, can be used in these assays. Thus, the antibodies can be used in a conventional immunoassay, including, without limitation, an ELISA, an RIA, FACS, tissue immunohistochemistry, Western blot or immunoprecipitation.

Numerous other assay protocols exist that are suitable for to detect sc-kit in a pregnant subject. The above descriptions are intended to be illustrative only.

The following examples are provided to illustrate certain particular features and/or embodiments. These examples should not be construed to limit the disclosure to the particular features or embodiments described.

EXAMPLES

Properly functioning vascular endothelial cells—the cells that line the interior of blood vessels—are vitally important for healthy cardiovascular function and healthy pregnancy. Many lines of evidence indicate that endothelial cell dysfunction explains the vasoconstriction, activation of the coagulation cascade, and multi-organ damage that often occurs during preeclampsia. The mechanisms of endothelial dysfunction in preeclampsia, however, remain poorly understood (Roberts, *Semin. Reprod. Endocrinol.*, 16(1):5-15, 1998; Woelkers and Roberts, *Handbook of Hypertension*, Vol 21, New York: Elsevier; 126-162, 2000; Gammill et al., *Front. Biosci.*, 12:2383-2394, 2007; Germain et al., *Hypertension*, 49:1-6, 2007). In normal pregnancy, cytotrophoblast cells from the placenta invade the maternal spiral arteries, causing them to lose their smooth muscle and enabling the expansion of vascular capacity necessary to support fetal growth. In some, but not all, cases of preeclampsia, there is insufficient remodeling of the spiral arteries, resulting in reduced utero-placental perfusion. Compromised utero-placental perfusion is thought to lead to the release of signals, many unidentified, from the placenta into the maternal circulation that target the maternal vascular endothelium. In women who develop preeclampsia, the downstream effects include widespread inflammation and endothelial cell dysfunction (Roberts and Hubel, *Lancet*, 354:788-789, 1999; Redman et al., *American Journal of Obstetrics & Gynecology*, 180(2 Part 1); 499-506, 1999).

There is still a need for an effective method for the diagnosis or preeclampsia or eclampsia, and for methods that can be used to monitor the efficacy of treatment regimens for these disorders.

It is demonstrated herein that women with preeclampsia are distinguished by abnormally low concentrations of sc-kit in maternal or umbilical cord (fetal) blood compared to both controls with uncomplicated (normotensive) pregnancies and women with just gestational hypertension without proteinuria or other hallmark signs of preeclampsia, and that maternal plasma sc-kit concentrations are reduced early in pregnancy (~18 weeks' gestation) in women who subsequently develop preeclampsia.

Example 1

Methods

Samples.

Archived plasma samples were obtained from the Preeclampsia Program Project (PEPP) longitudinal and cross-sectional studies of pregnant women enrolled at their first prenatal visit and followed through the immediate postpartum period. Clinical data was deidentified. A jury of clinicians met monthly to determine pregnancy diagnosis of all the women. The symptoms of Preeclampsia are: 1) new onset hypertension, plus 2) having proteinuria, plus 3) manifesting hyperuricemia (uric acid in serum greater than 1 standard deviation from normal for gestational age) with reversal of hypertension and proteinuria postpartum (Chesley, *Kidney Int*, 18:234-240, 1980). Uncomplicated pregnancy controls are normotensive, without proteinuria or hyperuricemia throughout gestation, and delivered of healthy babies at term. All participants were without illicit drug use, and had no history of renal or vascular disease.

Cross-Sectional Study:

Women with preeclampsia develop the disease and deliver at an earlier gestational age on average compared to women with gestational hypertension without proteinuria. Therefore, women with preeclampsia and women with gestational hypertension were group-matched to separate control groups according to the gestational age at the time of venipuncture. Thus, soluble sc-kit and stem cell factor (SCF; also known as kit-ligand) were compared in third trimester plasma samples from 26 women with preeclampsia (mean±SD gestational weeks at venipuncture: 34.1±3.0) matched to 27 controls (34.6±2.7 weeks; P=0.49) and 12 women with gestational hypertension (39.1±1.9 weeks) matched to 10 controls (39.1±1.9 weeks; P=0.99).

Concentrations of SCF are significantly higher in cord blood and neonatal blood than in the maternal blood, and strikingly high SCF mRNA expression and moderate c-kit mRNA expression is found in human umbilical vein (fetal) endothelial cells. Without being bound by theory, this suggests that endothelial cells are an important source of SCF in cord blood (perhaps during development of the fetoplacental vasculature and blood flow). If kit/SCF dysregulation exists in the fetoplacental circulation, this might be of pathophysiologic significance. Therefore, SCF and sc-kit were measured in cord blood samples that were available from a subset of these patients (n=19 preeclamptic pregnancies and n=22 control pregnancies).

Longitudinal Study:

Maternal nonfasting plasma samples were collected at the first prenatal visit and during pregnancy at usual times for clinical indications, and were stored in aliquots at −70° C. Sc-kit concentrations were measured in a 2:1 (case:control) study of gestational age-matched plasma samples obtained at mid-gestation (mean±SD gestational weeks: 18.7±2.3), prior to development of preeclampsia. The mid-pregnancy samples were obtained from 26 women who later developed preeclampsia and from 52 controls whose pregnancies remained uncomplicated. Of these women, samples were also available from 24 during clinically evident preeclampsia and 46 of the controls (gestational age-matched, third trimester samples).

Additionally, the change in plasma levels of sc-kit in subjects experiencing a normal pregnancy (non-preeclamptic/eclamptic) over the course of gestation, was assayed in longitudinal samples collected at 4 gestational windows (weeks 5-10, 16-19, 27-30, and 40-42 (pre-delivery)) from 9 controls with uncomplicated pregnancy outcome.

Postpartum Study:

The persistence (or reemergence) of deficits in circulating sc-kit after pregnancy was also explored. Study participants gave permission to be contacted for additional preeclampsia-related research studies upon consenting to participate. The women were mostly moderate- to low-income, and were a racially diverse population. Subjects underwent a history and physical examination and a urine pregnancy test. History of cardiovascular disease in any first-degree relative was recorded. Blood was collected on the morning after an overnight fast. Soluble c-kit and SCF were measured in the banked plasma from 21 primiparous women with a history of preeclampsia, 28 primiparous women with a history of normal pregnancy (both on average 1 year postpartum) and from 23 nulligravid/never pregnant women. No women were taking oral contraceptives or lactating, and all were nonsmokers. There were insufficient numbers of pregnancy samples available from these women for comparison.

ELISA of sc-Kit (SCFsR) and SCF:

Concentrations (during pregnancy and postpartum) were estimated in duplicate using ELISA based assays purchased from R&D Systems (Minneapolis, Minn.). The human sc-kit samples available from R&D were used as controls. The ELISAs for use in pregnancy samples were validated by performing sample dilution and spike-recovery tests on separate pools of preeclampsia and normal pregnancy plasma (n=6 patient samples per pool) as done previously for sFlt-1 and PlGF (Shibata et al., *J. Clin Endocrinol Metab*, 90(8): 4895-4903, 2005). The intra-assay coefficients of variation for sc-kit and SCF in our pregnancy plasma samples, respectively, were 5.1 and 5.9%. To assess linearity of the assays, a pregnancy reference sample was diluted with appropriate calibrator diluent and then assayed. Percent observed/expected values of 1:2, 1:4 and 1:8 dilutions of both analytes approximated 100%, ranging from 91 to 114%. sc-kit concentrations in pools of normal pregnancy plasma were not appreciably affected by the addition of 2 ng/mL human recombinant SCF (R&D Systems, Minneapolis, Minn.) or by the addition of 50 ng/mL human recombinant sFlt-1 (R&D Systems, Minneapolis, Minn.).

Immunoprecipitation of sc-kit was performed followed by Western analysis of sc-kit in pools of plasma collected from women experiencing a normal pregnancy and women with preeclampsia. Two pools of plasma (200 µL, pooled from n=4 women with preeclampsia and n=4 women having normal pregnancy) were diluted to 0.5 ml with sterile PBS and mixed with equal volume of 2× buffer, in the presence of protease and phosphatase inhibitors. To this 1 ml sample, 20 µL of protein A/G sepharose was added to pre-clear any non-specific proteins. The protein A/G agarose was then removed by centrifugation. 10 µL of the human specific anti c-kit (SCF-R; CD117, c-kit) antibody (R&D Systems, Minneapolis, Minn.) was added to the supernatant and incubated overnight at 4° C. These samples were further incubated for an additional 30 minutes with protein A/G sepharose and the immune complexes were captured and washed by centrifugation. The immunoprecipitated proteins were solubilized in 1× Laemmli buffer and subjected to electrophoresis followed by Western analysis using three different antibodies: 1) the same R&D Systems antibody used in the previous immunoprecipitation step, 2) a c-kit antibody from Santa Cruz Biotechnology (Santa Cruz, Calif.) and 3) a c-kit antibody from eBioscience (San Diego, Calif.).

As an additional validation of the R&D ELISA for sc-kit, aliquots (750 750 µg) of the pools of preeclampsia and normal plasma were immunoprecipitated with an antibody raised against the full-length c-kit (0.2 µg/ml, Santa Cruz Biotechnology catalog #sc-13508, Santa Cruz, Calif.). The immunocomplex was recovered using protein G sepharose beads. The precipitated proteins were released by the addition of 0.25 M glycine followed by neutralization with Tris buffer (pH 8.0). The released protein was added to the ELISA plate and allowed to bind. The antigen-antibody complex was eluted with 0.25 M glycine and the eluate was run on SDS-PAGE and the gel was re-probed with a mouse anti-human monoclonal antibody against c-kit (Santa Cruz, sc-13508).

Statistics:

The natural logarithm of data was used in cases in which plasma analyte concentrations were non-normally distributed. Data were analyzed by ANOVA or Student's unpaired t-test where appropriate. The three groups in the postpartum study were compared by ANOVA, with Bonferroni correction for multiple comparisons. Statistical significance was accepted at $p<0.05$.

Example 2

Cross-Sectional Study

Pilot data had indicated that lower concentrations of the soluble (circulating) receptor sc-kit exist in maternal plasma of women with preeclampsia compared to either controls with uncomplicated (normotensive) pregnancies or women with just gestational hypertension without other signs of preeclampsia. However, a general decline in plasma sc-kit concentrations was also observed with advancing gestational age. Women with preeclampsia develop the disease and deliver at an earlier gestational age on average compared to women with gestational hypertension without proteinuria. The number of patients was therefore expanded in this cross-sectional study during the third trimester; matching women with preeclampsia and women with gestational hypertension to separate control groups according to the gestational age at the time of venipuncture. Thus, soluble sc-kit and stem cell factor (SCF; also known as kit-ligand) were compared in plasma from 26 women with preeclampsia gestational age matched to 27 controls, and 12 women with gestational hypertension matched to 10 controls (39.1±1.9 weeks; P=0.99). Patients with preeclampsia delivered earlier ($p<0.001$), had babies with lower birth weights ($p<0.01$) and birth weight centiles ($p<0.01$), and by definition had higher blood pressure at admission to labor and delivery ($p<0.001$).

Figure 2:
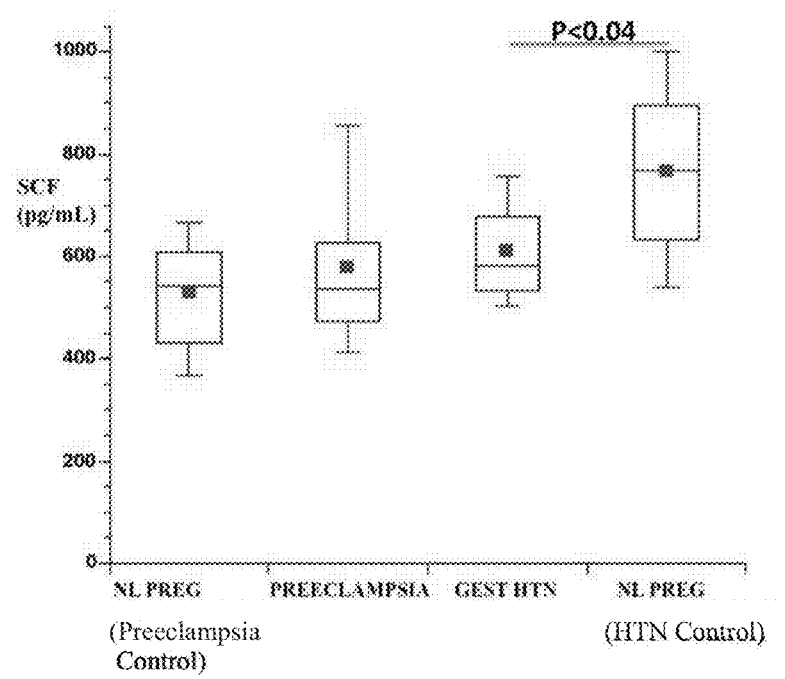
FIG. 2 is a graph showing the results of a cross-sectional study using ELISA to compare the concentration of SCF in women diagnosed with preeclampsia and diagnosed with gestational hypertension (GEST HTN). Concentration of SCF in women who had normal pregnancies is also shown (NL-PREG) as respective gestationally-matched controls for the preeclamptic and hypertensive test groups.

Concentrations of sc-kit were significantly lower in women with preeclampsia compared to controls ($P<0.0005$) whereas no difference in sc-kit was observed between gestational hypertensives and their controls (P=0.84) (FIG. 1). Concentrations of sc-kit were lower in the controls for gestational hypertension than controls for preeclampsia, reflecting the later gestational age of the former control group (FIG. 1). In contrast to sc-kit, no group differences were observed for plasma SCF except, surprisingly, for lower concentrations of SCF in women with gestational hypertension compared to their controls (P<0.04; FIG. 2).

Figure 3:
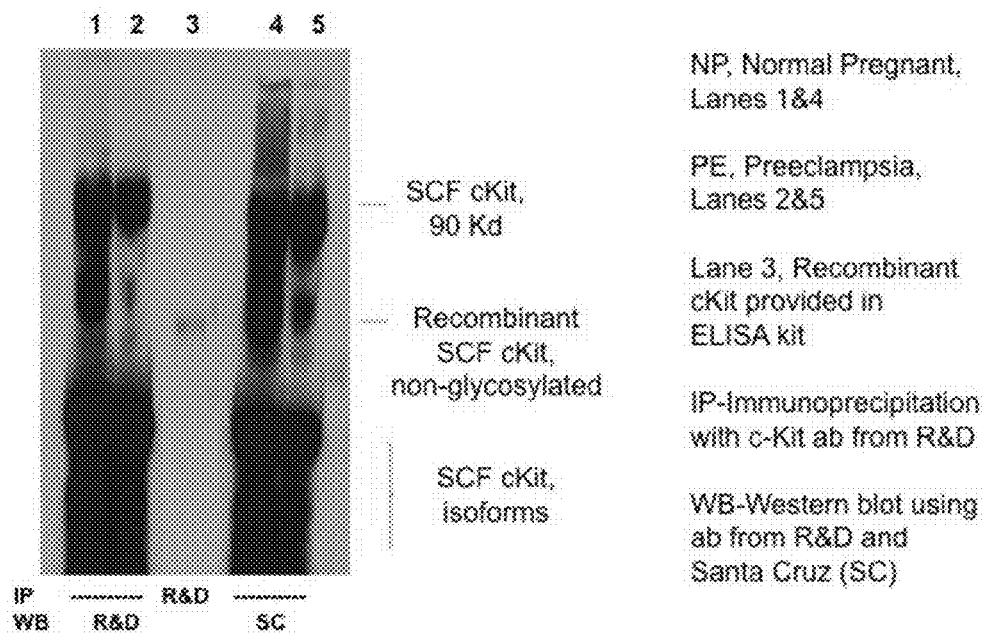
FIG. 3 is a Western blot showing sc-kit immunoprecipitated from samples taken from women who had normal pregnancies (NP; lanes 1 and 4) and who were diagnosed with preeclampsia (PE; lanes 2 and 5). Lane 3 is a control showing recombinant sc-kit. The immunoprecipitation (IP) was carried out with a c-kit antibody from R&D Systems (Minneapolis, Minn.) (R&D). The Western blot (WB) used c-kit antibodies from R&D and Santa Cruz Biotechnology Inc. (Santa Cruz, Calif.) (SC).

The ELISA results were corroborated by immunoprecipitation analysis. The three antibodies used gave similar profiles. The R&D antibody profile is shown in FIG. 3, showing fainter bands in preeclampsia samples. Note: soluble c-kit molecular weight has previously been estimated as ~90 kDa.

As additional validation of the R&D ELISA, the antigen-antibody complex eluted from the ELISA plate showed bands on a Western blot using an anti-sc-kit primary antibody from Santa Cruz Biotechnology Inc. (Santa Cruz, Calif.) corresponding to the correct molecular weight for sc-kit that were less pronounced in lanes corresponding to the preeclampsia pooled plasma compared to normal pregnancy plasma.

Concentrations of sc-kit are reportedly lower in non-pregnant women with systemic lupus erythematosus compared to healthy controls, partly attributable to the corticosteroid treatment that these patients receive (Kitoh et al., *Clin Reheumatol*, 17:293-300, 1998). In the current study, 15 of 26 women with preeclampsia and 1 control received injections of betamethasone prior to blood sampling. The 11 preeclamptics without betamethasone nevertheless had significantly lower plasma sc-kit concentrations than controls without betamethasone (P<0.04). The gestational age of preeclamptics who had not received betamethasone (mean 36.6 weeks, probably reflecting milder disease of later onset) was greater than preeclamptics who did receive the corticosteroid (mean 32.2 weeks) (P<0.0005) but sc-kit concentrations were not significantly different between the subgroups of preeclamptics who did versus did not receive betamethasone (P=0.34). SCF concentrations were not different between these betamethosone +/− subgroups. No gestational hypertensives in our patient sample received betamethasone.

Figure 4:
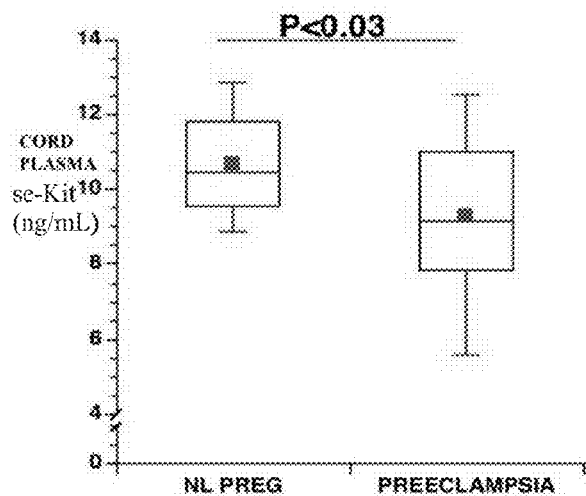
FIG. 4 is a graph comparing the concentration of sc-kit in umbilical cord (fetal) plasma of preeclamptic pregnancies and normal pregnancies (NL-PREG). Concentration of sc-kit was determined by ELISA.
Figure 5:
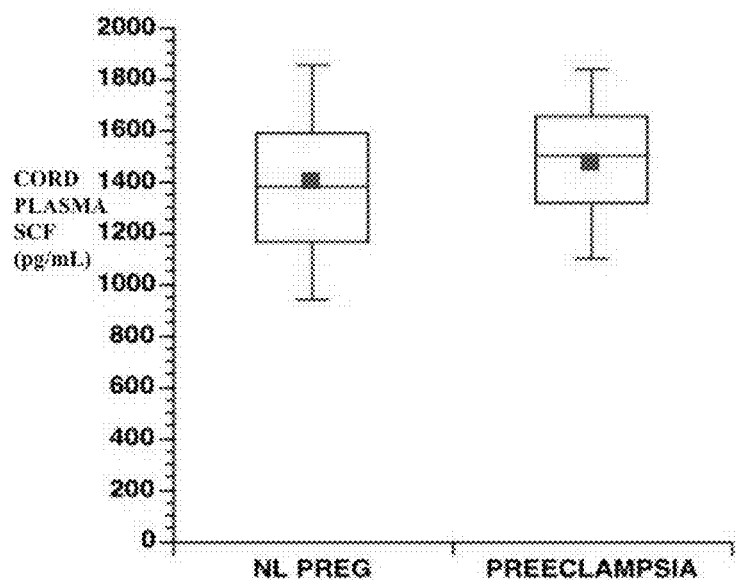
FIG. 5 is a graph comparing the concentration of SCF in umbilical cord (fetal) plasma of preeclamptic pregnancies and normal pregnancies (NL-PREG). Concentration of SCF was determined by ELISA.

Correlations were also explored between sc-kit or SCF and between plasma concentrations of free placental growth factor (PlGF, a pro-angiogenic factor) and soluble fms-like tyrosine kinase-1 (sFlt-1; also known as soluble VEGF receptor-1, an anti-angiogenic factor increased in most women with preeclampsia that binds and thus neutralizes VEGF and PlGF). Except for a weak positive correlation of SCF with sFlt-1 (r=0.41, P<0.05) among women with preeclampsia, no correlations were observed within any of the disease or control groups (including betamethasone +/− subgroups). Consistent with several previous studies, sFlt-1 was significantly elevated and PlGF reduced in women with preeclampsia, but not women with gestational hypertension, compared to controls. As with the maternal circulation, concentrations of sc-kit were significantly lower in umbilical cord (fetal) plasma from preeclamptic pregnancies (n=19) compared to control pregnancies (n=22) (P<0.03; FIG. 4). As with the maternal values, cord concentrations of SCF did not differ between preeclampsia and control groups (P=0.28; FIG. 5). Consistent with previous reports, however, fetal SCF concentrations were significantly higher in cord than maternal blood (compare FIGS. 2 and 5).

Example 3

Longitudinal Study

Figure 6:
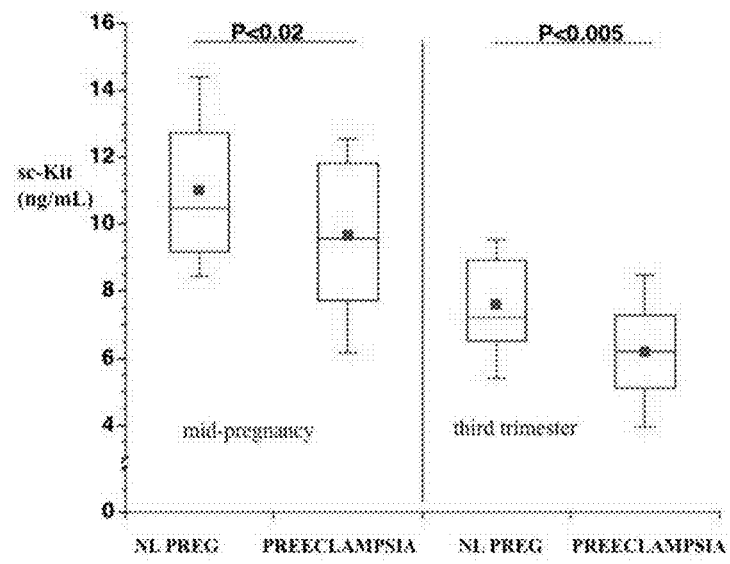
FIG. 6 is a graph showing the results of a longitudinal study using ELISA to compare the concentration of sc-kit in women having preeclamptic and normal pregnancies (NL-PREG). The concentration of sc-kit was determined at mid-pregnancy (mean±SD gestational weeks: preeclampsia 18.7±2.5, control 18.8±2.7; left) and in the third trimester (mean±SD gestational weeks: preeclampsia 37.3±4.2, control 37.0±4.2; right).

Similar to the cross-sectional study subjects, longitudinal subjects who developed preeclampsia delivered earlier (p<0.001), had lower birth weight babies (p<0.001) and birth weight centiles (p<0.01), and by definition significantly higher blood pressure at admission to labor and delivery (p<0.001). Plasma sc-kit concentrations were significantly reduced, both at 18 weeks (prior to clinically evident preeclampsia) (P<0.02) and during the third trimester (during the clinical syndrome) (P<0.005) in women who developed preeclampsia compared to controls (FIG. 6).

Figure 7:
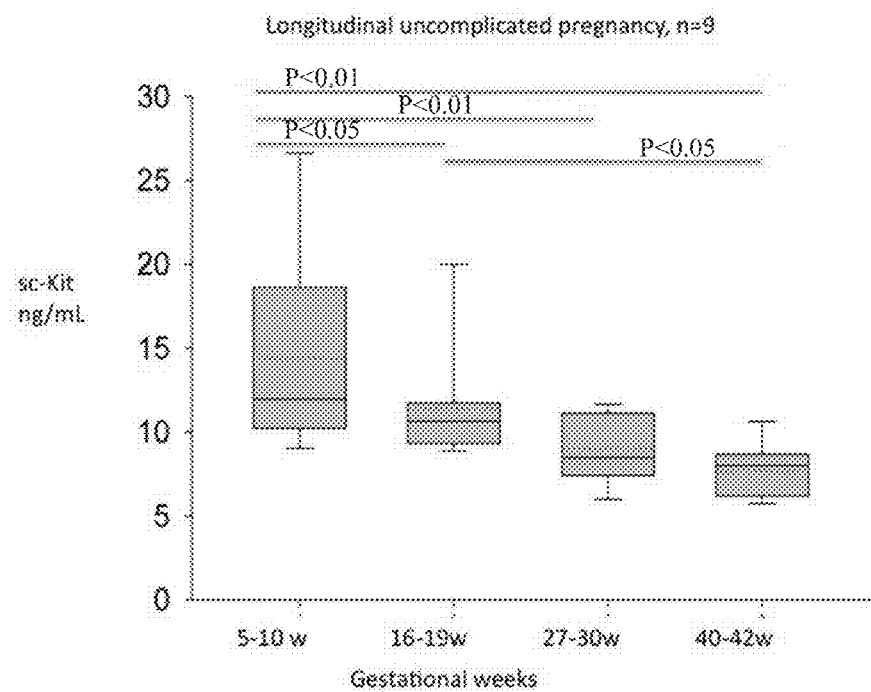
FIG. 7 is a graph showing the results of a longitudinal study using ELISA to monitor the concentration of sc-kit at several gestational time points in women having normal pregnancies.
Figure 8:
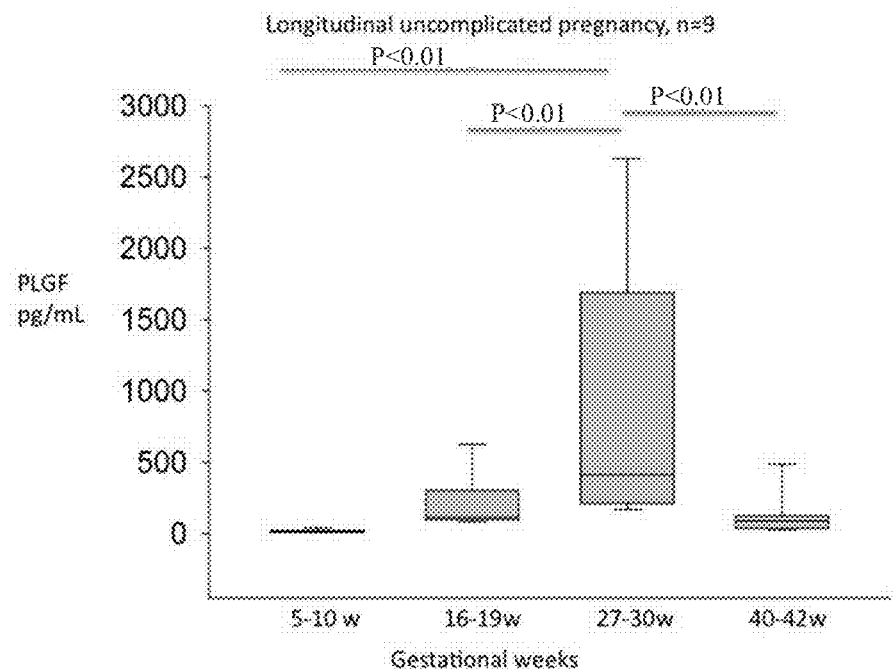
FIG. 8 is a graph showing the results of a longitudinal study using ELISA to compare the concentration of PlGF at several gestational time points in women having normal pregnancies.
Figure 9:
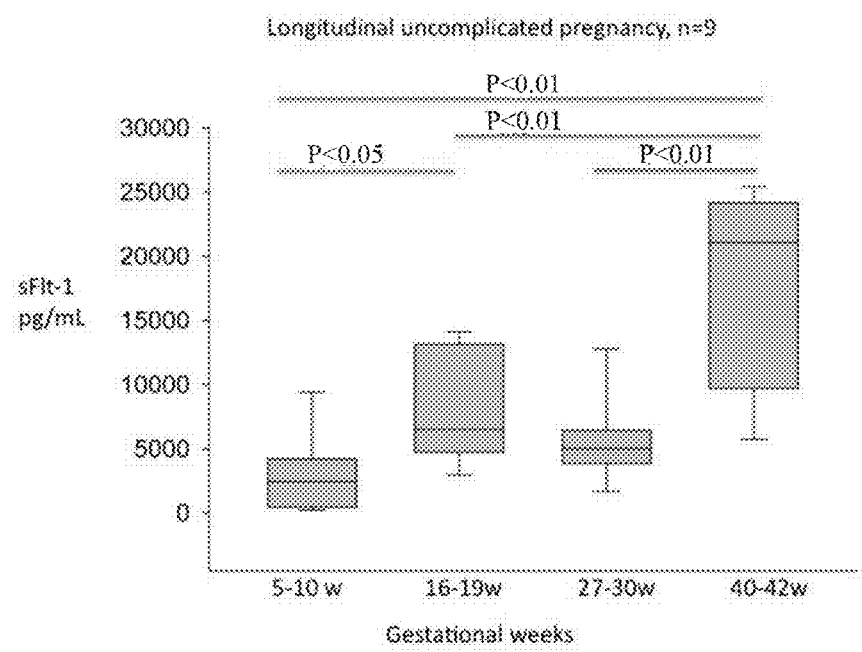
FIG. 9 is a graph showing the results of a longitudinal study using ELISA to compare the concentration of sFlt-1 at several gestational time points in women having normal pregnancies.

FIG. 7 shows that sc-kit concentrations decreased progressively over the course of uncomplicated pregnancy. Significant decreases occurred at the 16-19-, 27-30- and 40-42-week intervals compared to the 5-10 week interval, and between the 16-19 and 40-42 weeks' gestation intervals. FIG. 8 confirms previous reports that plasma PlGF increases during the first 30 weeks of gestation and then declines remarkably at term. Significant differences were found between the apparent apex at weeks' 27-30 and gestational weeks 5-10, 16-19 and 40-42. In contrast to sc-kit, sFlt-1 concentrations rose over the course of gestation, except for an apparent plateau at 27-30 weeks (FIG. 9). Significant correlations between sc-kit and PlGF were observed at gestational ages 16-19 (r=0.70, P=0.03) and 27-30 (r=0.65, P=0.05), but no other correlations of the three plasma variables within any of the other time points were observed.

Example 4

Postpartum Study

Persistence (or reemergence) of deficits in circulating sc-kit postpartum after first pregnancy was also tested. Soluble c-kit and SCF were measured in the banked plasma from 21 women with a history of preeclampsia, 28 women with a history of normal pregnancy (both on average 1 year postpartum) and from 23 nulligravid/never pregnant women. Mean systolic blood pressures in postpartum women with prior preeclampsia were slightly but significantly elevated (mean 119/78) compared to both women with prior normal pregnancy (110/71) (P<0.02 systolic and diastolic) and women who had never been pregnant (108/69) (P=0.01 systolic, P<0.002 diastolic). Body mass index (BMI) did not differ between the postpartum prior preeclamptic (mean 29.2 kg/m2) and normal pregnancy (28.1 kg/m2) groups, but each had significantly higher BMIs compared to the nulligravidas (23.5 kg/m2) (P<0.05). Mean heart rates, age, and days after delivery did not differ. Contrary to hypothesis, no between-group differences in sc-kit or SCF were observed.

Thus, it is demonstrated herein that dysregulated soluble c-kit is associated with preeclampsia. Given the normal sc-kit concentrations in women with gestational hypertension without proteinuria, the lower sc-kit concentrations in women with preeclampsia is not merely a consequence of hypertension per se. These data indicate that preeclampsia and gestational hypertension (without proteinuria) are distinct syndromes with different pathophysiology. The lack of correlation of sc-kit with sFlt-1 or PlGF suggests that sc-kit regulation is independent of sFlt-1 and PlGF (suggesting the possible utility of diagnostic or predictive rules that combine these variables). Without being bound by theory, sc-kit/SCF dysregulation exists in the fetoplacental circulation and thus may be of pathophysiologic significance. Low sc-kit could impact the fetus and fetal side of the placenta.

Median plasma sc-kit concentrations were significantly lower weeks before the onset of preeclampsia. Thus, sc-kit may have a role in the onset and progression of preeclampsia. These data thus support that reduced maternal plasma sc-kit concentrations are reduced early in pregnancy in many women who subsequently develop preeclampsia compared to women whose pregnancies remain uncomplicated. The postpartum data suggest that the lower sc-kit evidently associated with preeclampsia is a pregnancy-specific abnormality. Thus, without being bound by theory, sc-kit probably does not contribute to the increased risk of later-life cardiovascular disease in women with a history of preeclampsia.

Example 5

Prediction and/or Diagnosis of Preeclampsia/Eclampsia by Measurement of sc-Kit

As discussed above, the concentration of sc-kit in serum obtained from a pregnant subject is significantly reduced in preeclamptic pregnant subjects compared to normal pregnancies. This example discusses a method of predicting and/or diagnosing preeclampsia/eclampsia in pregnant subjects.

Prediction or diagnosis of preeclampsia/eclampsia involves measurement of sc-kit in a blood, plasma, or serum sample taken from a pregnant subject. A blood sample or plasma sample is taken from a human subject who is 20 weeks pregnant. The concentration of sc-kit in the blood sample or plasma sample is determined by use of an ELISA. The sc-kit concentration in the sample from the pregnant subject is compared to the sc-kit concentration that was measured in the blood of a subject who was 20 weeks pregnant and who did not have or develop preeclampsia. Alternatively the sc-kit concentration in the test subject is compared to a standard value of sc-kit for non-preeclamptic/non-eclamptic pregnant subjects at 20 weeks. A statistical test is performed. A statistically significant reduction in the sc-kit in the blood sample from the test pregnant subject in comparison to the control subject or standard value is predictive of preeclampsia if the subject does not have any preeclampsia symptoms, or indicative of preeclampsia after development of symptoms. If the subject is partially symptomatic, such as hypertensive, but without proteinuria, a statistically significant reduction in sc-kit concentration compared to the control subject or standard value indicates that the pregnant subject is likely to develop preeclampsia (gestational hypertension with proteinuria) later in the pregnancy.

Example 6

Diagnostic Test for Diagnosing Preeclampsia or Eclampsia

This example describes an exemplary diagnostic test, for example in a clinical setting, for detecting preeclampsia or eclampsia in a subject. However, one skilled in the art will appreciate that methods that deviate from these specific methods can also be used to successfully detect preeclampsia or eclampsia.

In some embodiments, the test includes directly determining an amount of sc-kit in a sample in a subject, for example a bodily fluid such as a blood, serum, or plasma sample, for example as described in Example 1. The results of the test are provided to a user (such as a clinician or other health care worker, laboratory personnel, or patient) in a perceivable output that provides information about the results of the test. In some examples, the output can be a paper output (for example, a written or printed output), a display on a screen, a graphical output (for example, a graph, chart, voltammetric trace, or other diagram), or an audible output. In one example, the output is one or more voltammetric traces obtained utilizing an electrochemical immunoassay, such as a AuNP immunosensor. The size of the voltammetric trace is proportional to the amount of sc-kit protein in the sample.

In other examples, the output is a numerical value, such as an amount of sc-kit protein in the sample or a relative amount of sc-kit protein in the sample as compared to a control. In additional examples, the output is a graphical representation, for example, a graph that indicates the value (such as amount or relative amount) of sc-kit protein in the sample from the subject on a standard curve. In a particular example, the output (such as a graphical output) shows or provides a cut-off value or level that indicates the presence of preeclampsia or eclampsia if the value or level of sc-kit protein in the sample is below the cutoff and absence of preeclampsia or eclampsia if the value or level of sc-kit protein in the sample is above the cut-off. In some examples, the output is communicated to the user, for example by providing an output via physical, audible, or electronic means (for example by mail, telephone, facsimile transmission, email, or communication to an electronic medical record).

The output can provide quantitative information (for example, an amount of sc-kit protein or an amount of sc-kit protein relative to a control sample or value) or can provide qualitative information (for example, a diagnosis of presence or absence of preeclampsia or eclampsia, a likelihood of developing preeclampsia or eclampsia, or information as to whether the subject has preeclampsia or eclampsia or gestational hypertension). In additional examples, the output can provide qualitative information regarding the relative amount of sc-kit protein in the sample, such as identifying a reduction in sc-kit protein relative to a control or no change in sc-kit protein relative to a control.

In some examples, the output is accompanied by guidelines for interpreting the data, for example, numerical or other limits that indicate the presence or absence of preeclampsia or eclampsia. The guidelines need not specify whether preeclampsia and/or eclampsia is present or absent, although it may include such a diagnosis. The indicia in the output can, for example, include normal or abnormal ranges or a cutoff, which the recipient of the output may then use to interpret the results, for example, to arrive at a diagnosis, prognosis, or treatment plan. In other examples, the output can provide a recommended therapeutic regimen (for example, based on the amount of sc-kit or the amount of decrease of sc-kit relative to a control).

In some examples, the test may include determination of other clinical information (such as determining blood pressure, or measuring the presence of other proteins in the sample). In some examples, the test includes an array, such as an antibody array or an electrochemical immunosensor array and the output of the test includes quantitative or qualitative information about sc-kit protein (such as the amount of sc-kit protein or an amount of change of sc-kit protein relative to a control, or a relative increase or decrease of sc-kit protein compared to the control), as well as quantitative or qualitative information about one or more additional proteins.

Example 7

Combination Methods to Predict or Diagnose Preeclampsia/Eclampsia

As disclosed herein, a significant reduction in sc-kit concentration in pregnant subjects is predictive or indicative or preeclampsia/eclampsia. It has previously been shown that an increase in sFlt-1 or soluble endoglin, or a reduction in PlGF or circulating EPCs can also be predictive or indicative of preeclampsia/eclampsia. Thus, the predictive value of sc-kit measurement can be enhanced by combining the measurement of sc-kit with the measurement of one or more of sFlt-1, soluble endoglin, PlGF, or circulating EPCs. This example presents a method of predicting or diagnosing preeclampsia/eclampsia in a pregnant subject that combines the measurement of sc-kit as well as one or more of sFlt-1, soluble endoglin, PlGF, or circulating EPCs.

A blood sample is taken from a human subject who is 20 weeks pregnant. The concentrations of sc-kit and at least one of sFlt-1, soluble endoglin, PlGF, or circulating EPCs in the blood sample are determined by use of separate ELISAs that are specific for each factor. The concentration of circulating EPCs is determined by detection of one or more EPC-specific cell surface markers CD34, CD133, the vascular endothelial growth factor receptor-2 (VEGFR-2), or CD31. The concentrations of sc-kit and at least one of sFlt-1, soluble endoglin, PlGF, or circulating EPCs in the pregnant subject are compared to the concentrations of sc-kit and at least one of sFlt-1, soluble endoglin, PlGF, or circulating EPC concentration that were measured in the blood of a subject who was 20 weeks pregnant and who did not have or develop preeclampsia. A significant reduction in the sc-kit concentration combined with a significant increase in sFlt-1 or soluble endoglin and/or a significant reduction in PlGF or circulating EPCs in the test pregnant subject will be predictive of preeclampsia if the subject does not have any preeclampsia symptoms, or indicative of preeclampsia after development of symptoms.

Example 8

Monitoring the Efficacy of Preeclampsia/Eclampsia Treatment by Measurement of sc-Kit Significantly reduced concentrations of sc-kit in a pregnant subject are indicative of preeclampsia/eclampsia. This example describes a method of monitoring the efficacy of preeclampsia/eclampsia treatment by measurement of sc-kit.

In this example, the concentration of sc-kit in the blood of a subject is determined and compared to a gestationally-matched control or standard value as described in any of the preceding examples. If the measured concentration of sc-kit in comparison to the control indicates that the subject has or is predictive of preeclampsia or eclampsia, appropriate clinical interventions are taken. Such interventions for preeclampsia/eclampsia include, but are not limited to, bed rest, administration of an antihypertensive medication, or administration of magnesium sulfate.

The methods described herein of monitoring the concentration of sc-kit are then used to monitor the efficacy of the prescribed preeclampsia/eclampsia intervention. For example, at regular intervals following prescription of the therapy, a blood sample or serum sample is obtained from the preeclamptic/eclamptic subject and the concentration of sc-kit in the blood sample is determined by an assay, such as an ELISA, and compared to a control, such as the concentration of sc-kit in the preeclamptic/eclamptic subject prior to prescription of the therapy or a gestationally-matched control value or gestationally-matched standard value of sc-kit in a subject known to be experiencing a normal pregnancy.

A significant increase in or attenuation in the reduction of sc-kit concentration in the subject over the course of the prescribed therapy indicates the therapy is effective. The therapy can be adjusted based on the results of the assay. Thus, if there is not a significant increase in or attenuation in the reduction of sc-kit, a different therapeutic agent can be administered to the subject. If there is a significant increase in or attenuation in the reduction of sc-kit, the therapy can be continued.

It should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for diagnosing preeclampsia or eclampsia in a pregnant subject, or for distinguishing preeclampsia or eclampsia from gestational hypertension in a pregnant subject, the method comprising:
   (a) quantitating soluble c-kit in a sample obtained from the pregnant subject, wherein the sample is a blood, plasma or serum sample;
   (b) quantitating soluble fms-like tyrosine kinase-1 or free placental growth factor in the sample;
   (c) detecting a statistically significant decrease in the concentration of soluble c-kit in the sample as compared to a control, wherein the control is a level of soluble c-kit in a sample from a gestationally matched pregnant subject that does not have eclampsia or pre-eclampsia; and
   (d) detecting a statically significant elevation in soluble fms-like tyrosine kinase-1, a statistically significant reduction in free placental growth factor, or both, in the sample as compared to a control, wherein the control is a level of fms-like tyrosine kinase-1 or free placental growth factor respectively, from a gestationally matched pregnant subject that does not have eclampsia or pre-eclampsia,
   wherein the combined detection in step (c) and step (d) indicates that the pregnant subject has preeclampsia or eclampsia, or indicates that the pregnant subject has preeclampsia or eclampsia and does not have gestational hypertension.

2. The method of claim 1, wherein the pregnant subject is a veterinary subject.

3. The method of claim 1, wherein the pregnant subject is a human subject.

4. The method of claim 3, wherein the pregnant subject is in the second or third trimester of pregnancy.

5. The method of claim 4, wherein the pregnant subject is at least eighteen weeks pregnant.

6. The method of claim 1, wherein the sample is a maternal blood, plasma, or serum sample.

7. The method of claim 1, wherein the sample is an umbilical cord blood, plasma, or serum sample.

8. The method of claim 1, wherein quantitating soluble c-kit comprises:
   contacting the sample with an antibody that specifically binds soluble c-kit, under conditions sufficient for the antibody to form an immune complex with soluble c-kit, and
   determining the quantity of the immune complex.

9. The method of claim 8, wherein the antibody is labeled.

10. The method claim 9, wherein the label is a radioisotope.

11. The method claim 9, wherein the label is an enzyme.

12. The method of claim 8, if wherein quantitating comprises the use of radioimmunoassay.

13. The method of claim 8, wherein quantitating comprises the use of an enzyme-linked immunosorbent assay (ELISA).

14. The method of claim 1, further comprising treating the pregnant subject for preeclampsia or eclampsia.

15. The method of claim 14, wherein treating the subject comprises prescribing bed rest or administering a therapeutic agent.

16. The method of claim 1, further comprising measuring the blood pressure of the pregnant subject, detecting proteinuria in the pregnant subject, or both.

17. A method for diagnosing preeclampsia or eclampsia in a pregnant subject, or for distinguishing preeclampsia or eclampsia from gestational hypertension in a pregnant subject, the method comprising:
   (a) quantitating soluble c-kit in a sample obtained from the pregnant subject;
   (b) quantitating circulating endothelial progenitor cells in the sample from the subject,
   wherein the sample is a blood, plasma or serum sample;
   (c) detecting a statistically significant decrease in the concentration of soluble c-kit in the sample as compared to a control, wherein the control is a level of soluble c-kit in a sample from a gestationally matched pregnant subject that does not have eclampsia or preeclampsia; and
   (d) detecting a statistically significant reduction in circulating endothelial progenitor cells compared with a control, wherein the control is a level of circulating endothelial cells in a sample from a gestationally matched pregnant subject that does not have eclampsia or preeclampsia,
   wherein the combined detection in step (c) and step (d) indicates the pregnant subject has preeclampsia or eclampsia or indicates that the pregnant subject has preeclampsia or eclampsia and does not have gestational hypertension.

18. The method of claim 17, wherein quantitating circulating endothelial progenitor cells comprises
   contacting the sample with an antibody that specifically binds an endothelial progenitor cell marker, under conditions sufficient for the antibody to form an immune complex with an endothelial progenitor cell marker, and of quantitating the immune complex.

19. The method of claim 18, wherein quantitating circulating endothelial progenitor cells comprises flow cytometry.

20. The method of claim 17, wherein the circulating endothelial progenitor cells express CD34 and CD133.

21. The method of claim 17, wherein the subject is a human subject.

22. A method of diagnosing preeclampsia or eclampsia in a pregnant subject, or of distinguishing preeclampsia or eclampsia from gestational hypertension in a pregnant subject, the method comprising:
   (a) quantitating soluble c-kit in a sample obtained from the pregnant subject;
   (b) quantitating circulating endothelial progenitor cells, wherein the circulating endothelial progenitor cells express one or more of CD34, CD133, the vascular endothelial growth factor receptor-2 (VEGFR-2), and CD31
   wherein the sample is a blood, plasma or serum sample;
   (c) detecting a statistically significant decrease in the concentration of soluble c-kit in the sample as compared to a control, wherein the control is a level of soluble c-kit in a sample from a gestationally matched pregnant subject that does not have eclampsia or preeclampsia; and
   (d) detecting a statistically significant reduction in circulating endothelial progenitor cells compared with a control, wherein the control is a level of the circulating endothelial cells in a sample from a gestationally matched pregnant subject that does not have eclampsia or preeclampsia,
   wherein the combined detection in step (c) and step (d) indicates that the pregnant subject has preeclampsia or eclampsia or indicates that the pregnant subject has preeclampsia or eclampsia and does not have gestational hypertension.

* * * * *

UNITED STATES PATENT AND TRADEMARK OFFICE
CERTIFICATE OF CORRECTION

PATENT NO. : 8,518,716 B2
APPLICATION NO. : 12/955762
DATED : August 27, 2013
INVENTOR(S) : Hubel et al.

It is certified that error appears in the above-identified patent and that said Letters Patent is hereby corrected as shown below:

Title page:

On page 2 under (56) References Cited, in the Kitoh et al. reference, "*Reheumatol*" should be --*Rheumatol*--.

On page 2 under (56) References Cited, in the Mathew et al. reference, "2011." should be --2011).--.

In the Drawings:

Fig 4, page 2, "se-kit" should be --Sc-kit--.

In the Specification:

Column 1, line 50, "that while they" should be --that_they--.

Column 3, line 27, "Radioimmunoas say" should be --Radioimmunoassay--.

Column 4, line 19, "40% 50%" should be --40%, 50%--.

Column 4, line 27, "40% 50%" should be --40%, 50%--.

Column 4, line 55-56, "antibodies), heteroconjugate" should be --antibodies and/or heteroconjugate--.

Column 4, line 55-56, "such as...antibodies)." should be --(such as...antibodies).--.

Column 6, line 29, "subjects, who does not" should be --subjects who do not--.

Column 7, line 11, "sytolic" should be --systolic--.

Column 7, line 51-52, "include without limitation," should be --include, without limitation,--.

Column 7, line 57, "such one" should be --such as one--.

Column 8, line 36, "as a leucine zipper pair sequences," should be --as leucine zipper pair sequences--.

Signed and Sealed this
Eighth Day of December, 2015

Michelle K. Lee
*Director of the United States Patent and Trademark Office*

CERTIFICATE OF CORRECTION (continued)
U.S. Pat. No. 8,518,716 B2

Column 8, line 42-43, "Normotenisive" should be --Normotensive--.

Column 9, line 49, "accession number is NM" should be --accession number NM--.

Column 10, line 6-7, "cells particularly fibroblasts and" should be --cells, particularly fibroblasts, and--.

Column 10, line 8, "soluble from" should be --soluble form--.

Column 10, line 10, "protein sequences" should be --protein sequence--.

Column 10, line 35, "exlampsia" should be --eclampsia--.

Column 10, line 58, "soluble c-kit is a" should be --soluble c-kit in a--.

Column 11, line 6, "immunosorbant" should be --immunosorbent--.

Column 11, line 11-12, "endoglin; and/or or" should be --edoglin, and/or--.

Column 11, line 67, "from" should be --form--.

Column 12, line 31, "or diagnosis of," should be --or diagnosis, of--.

Column 12, line 47, "concentration or one or" should be --concentration of one or--.

Column 13, line 26, "gestationally matched" should be --gestationally-matched--.

Column 13, line 26, "subject" should be --subjects--.

Column 13, line 54, "regiment" should be --regimen--.

Column 13, line 65, "in effective" should be --is effective--.

Column 14, line 17-18, "recognizes" should be --recognize--.

Column 14, line 62, "exemplary a magnetic" should be --exemplary magnetic--.

Column 16, line 59-60, "factors the same" should be --factors of the same--.

Column 17, line 54, "Elsevier;" should be --Elsevier,--.

Column 18, line 2, "(2 Part 1);" should be --(2 Part 1),--.

Column 18, line 5, "diagnosis or" should be --diagnosis of--.

Column 20, line 17, "(750 750 μg)" should be --(750 μg)--.

Column 20, line 58-59, "age matched" should be --age-matched--.

Column 21, line 23-24, "Reheumatol" should be --Rheumatol--.

Column 21, line 37, "betamethosone" should be --betamethasone--.

Column 22, line 17, "weeks' 27-30" should be --weeks 27-30--.

Column 22, line 43, 45, "kg/m2)" should be --kg/m$^2$)--.

Column 22, line 52, "is not merely" should be --are not merely--.

Column 24, line 13, 38, "cutoff" should be --cut-off--.

Column 24, line 63, "or preeclampsia/" should be --of preeclampsia--.

In the Claims:

Column 26, line 27, "statically" should be --statistically--.

Column 26, line 60, 61, "the method claim" should be --the method of claim--.

Column 26, line 62, "if wherein" should be --wherein--.

Column 27, line 19, 24 and Column 28, line 24, 29, 30, "gestationally matched" should be --gestationally-matched--.